United States Patent

Cosman et al.

[11] Patent Number: 5,304,114
[45] Date of Patent: Apr. 19, 1994

[54] SHUNT VALVE SYSTEM

[76] Inventors: Eric R. Cosman, 872 Concord Ave., Belmont, Mass. 02178; Michael A. Arnold, 4 Rag Rock Dr., Woburn, Mass. 01801

[21] Appl. No.: 700,689

[22] Filed: May 15, 1991

[51] Int. Cl.$^5$ ............................................. A61M 5/00
[52] U.S. Cl. ............................................. 604/8; 604/9
[58] Field of Search ................ 604/8, 9, 10, 175, 185; 137/510

[56] References Cited

U.S. PATENT DOCUMENTS

| | | | |
|---|---|---|---|
| 3,827,439 | 8/1974 | Schulte et al. | 604/9 |
| 3,901,245 | 8/1975 | Spitz et al. | 604/10 |
| 4,364,395 | 12/1982 | Redmond et al. | 604/10 |
| 4,464,168 | 8/1984 | Redmond et al. | 604/9 |
| 4,552,553 | 11/1985 | Schulte et al. | 604/9 |
| 4,560,375 | 12/1985 | Schulte et al. | 604/9 |
| 4,588,394 | 5/1986 | Schulte et al. | 604/8 X |

Primary Examiner—Robert A. Hafer
Assistant Examiner—Sam Rimell
Attorney, Agent, or Firm—Richard J. Birch

[57] ABSTRACT

This invention relates to a CSF shunting system that can be used in the human body for the control of hydrocephalus or excess cerebrospinal fluid (CSF) in the ventricles of the brain. The invention relates to the configuration of a fluid pressure controlling diaphragm which has a substantially planar, non-arched, or slightly convex occluding surface that contacts as its valve mechanism a non-planar opposing surface. The diaphragm element can be made out of silicone rubber or some other flexible material, and the opposing surface can be made from a dissimilar material from the diaphragm element to prevent sticking. The invention also relates to the configuration of this substantially flat diaphragm element, its central stem, and its mounting in a frame so as to facilitate pre-loads, calibrations, and optical, as well as mechanical, tests for quality assurance. The invention further relates to a confirmation of this pressure control invention in a larger shunt body geometry, which provides for modular, distal, and occlusion elements, and articulating shape to better fit the contour of a patient's skull.

10 Claims, 2 Drawing Sheets

1

SHUNT VALVE SYSTEM

BACKGROUND TO THE INVENTION

The use of fluid shunting systems to shunt the cerebrospinal fluid (CSF) from the ventricles of the patient's brain to his heart or peritoneum in the treatment of hydrocephalus is common today. Many configurations of shunts and their indwelling pressure control elements have been invented, and the literature is full of their application experience. Many of these devices have membranes or diaphragm type pressure control elements whose characteristic gives a desired pressure flow curve for the CSF fluid that they are shunting. Relevant to the present invention are the shunt configurations of the Heyer-Schulte Company, which have a dome-shaped diaphragm pressure control element, and the Pudenz-Schulte Medical Company, which have an arched shape or mushroom-shaped pressure control element. These are described in their brochures and relate to the U.S. Pat. Nos. 4,364,395; 4,464,168; 4,552,553; and, 4,560,375. Furthermore, the Radionics Company has a shunt which uses a quasi-septum type pressure control element that has a silicone spoon-shaped member as one side of the occluding surface and a Teflon articulating member for the opposing side of the pressure control element. The silicone and the Teflon elements move and open relative to each other to allow passage of fluid under the application of a pressure differential across the element. These pressure control designs are functional, and each has advantages. Furthermore, they are embodied in a larger shunt configuration which involves either a unitized, contoured type base valve, exemplified by the Heyer-Schulte and the Pudenz-Schulte medical companies, which provide in one unitized construction a proximal occlusion, a dome structure for flushing or needling injection, a distal occluder, and a pressure control element with unitized nipple connectors on the proximal and distal end for connecting to the proximal and distal catheters of the shunt system. Descriptions of the use of this contoured or unitized shunt construction are given in the literature and in the brochures. Also in the patents cited above and in the literature there is discussion about how to use these valves and also how to fabricate, test, and perform quality assurance on these valves. Essential here is the method of pre-loading the diaphragm elements so that they will have a specific and reproducible pressure flow characteristic. In general, the description in the patents and the literature are based on stiffness of the diaphragm elements, variation in thickness, and topology of the diaphragm elements, pre-loading methods involving pre-loading and gluing the stems of mushroom-type diaphragm elements, and sample selection of lots and devices. It is also described in the Heyer-Schulte and PS Medical brochures that their contoured valve has a unitized inner platform or body which is made of a relatively hard material, such as polypropylene. This body has a predetermined shape or contour as one looks at it in side section, the idea being that this contour will match the contour of the patient's skull, which is relatively curved when the shunt is implanted. Throughout their literature and patents they teach the use of this firm body with distal and proximal ports for digital or manual flushing of the valve, either proximally or distally, by means of finger pressure on the occluder at either the proximal or distal end followed by pressure on the flexible dome reservoir to flush it. Proximal and distal flushing are also described in the function of the Radionics shunt.

It is an objective of the present invention to provide a shunt valve configuration which has separate proximal occlusion internal body and separate distal occlusion inner body so that the articulation of the shunt can conform to the individualized contour of the patient's skull, unlike the fixed body or unitized body design of Heyer-Schulte and Pudenz-Schulte companies.

Another objective of the present invention is to provide a substantially planar or somewhat convex diaphragm shape which occludes against a non-planar surface of different material to constitute the pressure flow controlling element and reflux control closing element. By means of such an essentially planar diaphragm configuration, together with a non-planar opposing surface, facilitation of testing can be done both visually and by pre-loading of the diaphragm stem or other structure.

DESCRIPTION OF THE INVENTION

Figure 1:
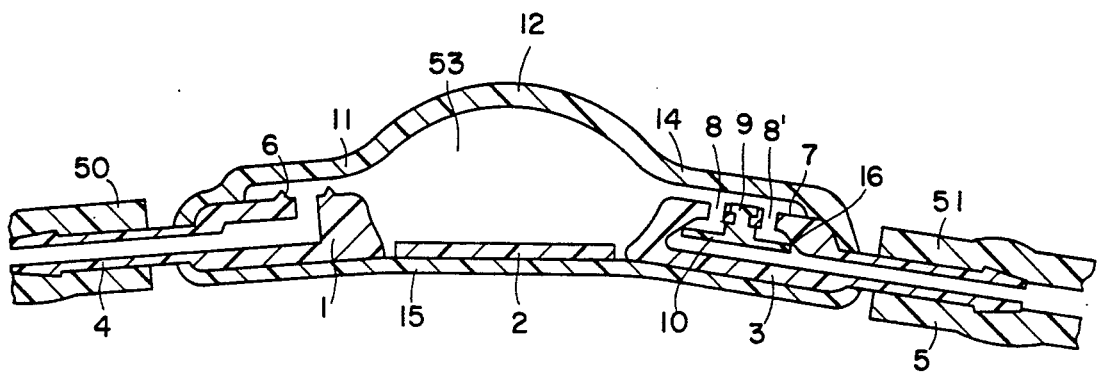
FIG. 1 shows a sectional view of the entire valve of the present invention in one embodiment in which the separate proximal and distal occluding ports are shown and the planar diaphragm are shown.

Referring to FIG. 1, this shows an elevation section view through one embodiment of the invention. On the so-called proximal end, which has the nipple connector 4, the shunt system is attached to the proximal tube, represented by 50. This may be a silicone tube which goes to the ventricles of the brain to access the CSF (cerebrospinal fluid) from the ventricles. The fluid will pass through the tubing 50 into the shunt system and through the port 6, which is made in the first body structure 1. This proximal body structure may be made out of a hard plastic such as polypropylene and be of integral construction with the nipple 4. The fluid passes through the port and then underneath the housing portion 11 above it. The overall housing, consisting of portion 11, dome 12, and distal portion 14 may be made out of a flexible silicone rubber. The CSF continues on into the inner dome space 53 underneath dome 12. It then continues into the region of the distal port represented by the structures 8, 8', 9, and the upper surface of the distal body 3. The distal body 16 may also be made of a hard plastic material such as polypropylene and also has a distal nipple 5. That distal nipple 5 is connected to a distal tubing 51 which shunts the CSF fluid onward toward the heart or the peritoneum, and thus relieves the pressure in the ventricles of the brain. Beneath the dome 12 there is another firm element 2 which may be a separate polypropylene structure and is there for the purpose of a backstop in case the surgeon injects a needle through the self-sealing rubber dome 12, preventing the needle from going any further into the outer table of the patient's skull. Such configurations of shunts, having a proximal entrance structure, an intermediate dome structure for injection or flushing, and of distal structure, are common.

One of the unique aspects of the present structure is that the proximal port system represented by 6, 4, and 1 are part of a separate firm body called the proximal body 1. This is mechanically decoupled from the firm base 2 and the distal firm body represented by 3 and the structures 8, 8', 9, and the distal connector 5. One of the objectives of the present invention is this mechanical decoupling of these firm port and base structures. This means that there can be an angular articulation, or contour change, of the proximal and distal bodies so that when the shunt is drawn under the scalp and above the skull of the patient, the proximal and distal bodies can flex relative to each other to conform to the patient's skull. That is to say that proximal body 1 and proximal body 3 can change their angle or contour relative to the skull because they are held together by the flexible silicone housing 11, 12, and 14 and the flexible lower backstop 15. 15 may also be made out of a silicone rubber, and thus sealed with the upper dome structures 11, 12, and 14.

In practice, a surgeon may press through the intact scalp over the shunt system onto the area of covering 11, thus depressing the flexible portion 11 over the port 6 so as to occlude flow at that point. He may then use a second finger to press the dome 12, and thus flush the fluid distally. Alternatively, he may press over the flexible portion 14 of the upper silicone housing, thus occluding the holes 8 and 8', which represent the distal port. He may then use a second finger, depress the dome 12, and thereby flush the fluid in the chamber space 53 proximally. This is a standard occlusion and flushing methodology used in shunts.

A second feature of the invention, illustrated in FIG. 1, is the pressure control element represented by the diaphragm 10 which is secured by its stem 9 into the structure of the distal body 3. The CSF fluid will flow through the holes 8 and 8' and when pressure builds up on the upper surface of the diaphragm 10, it will flex, thereby allowing the fluid to pass by the occluding surface 16 and on to the distal connector region 5. To describe in more detail the features of the distal body 3, the fluid after passing from chamber 53 enters the holes 8 and 8'. Build-Up of pressure on the proximal end, that is the end at the patient's head, will exert a force on the occluding face of diaphragm 10. The diaphragm is substantially flat in its configuration, and it occludes against the non-planar surface 16. The diaphragm is substantially a disk with a stem 9 that is affixed to a portion of the polypropylene base 3, which is shown in more detail in the figures below. Thus, the diaphragm element 10 acts as a pressure vent, or pressure control element. As the pressure builds up, the diaphragm opens more, more fluid passes through, thus relieving pressure in the brain and decreasing the pressure on the occluding surface of the diaphragm. The diaphragm, therefore, will open up and close down according to the differential pressure across it.

Figure 2:
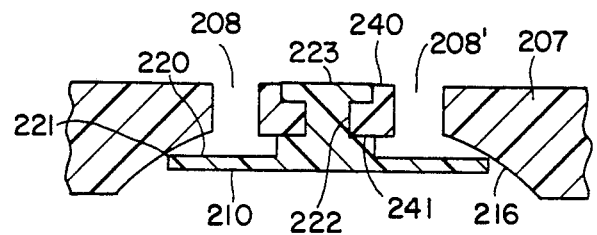
FIG. 2 shows a specific embodiment of the pressure control element, including the substantially planar diaphragm with the non-planar occluding and opposing surface.

FIG. 2 shows a more detailed view of the pressure control element of FIG. 1. In this figure the flat diaphragm 210 has on its upper surface the occlusion edge which meets the opposing occluding surface 216. 216 is part of the distal body 3, all of which is not shown. The fluid holes are 208 and 208'. The diaphragm is substantially flat and contacts the occluding surface along the line 221. The occluding surface of the diaphragm 220 is relatively flat, whereas the opposing occluding surface 216 is non-planar near the contact region. The diaphragm 210 has a stem section 222 which goes through an opening in the structure 240, which is part of the polypropylene distal base 3 in FIG. 1. The stem 222 has a flared portion 223 which is secured mechanically in the structure 240. The flared section may be molded permanently into the diaphragm element 210 and may be of such a geometry that it pre-stresses the diaphragm 210 against the occluding surface 216. This can also be arranged by the specific geometry of the shoulder 241 that presses against the element 240. Further details of biasing the diaphragm element will be discussed below.

Because the occluding surface 216 is non-planar, there will be no obstruction to fluid flow through the holes 208 and 208' to approximate the upper surface 220 or the diaphragm over all of its area. The occlusion line 221 assures that there is minimum surface area for particulant matter to obstruct the closure of the diaphragm 210 against the occluding surface 216. Variants of FIG. 2 are possible in which the diaphragm portion away from the occluding surface 216 is non-planar. It could be reinforced with ribs or be thickened towards the central axis to vary the pressure flow characteristics of the diaphragm.

Figure 3:
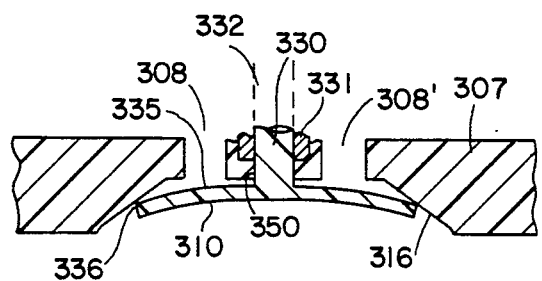
FIG. 3 shows a variation of the embodiment to FIG. 2 in which the pressure control diaphragm is somewhat convex as it faces the non-planar opposing and occluding surface.

FIG. 3 shows yet another embodiment of the pressure control portion of the present invention. It is similar to FIG. 2, except that the diaphragm element 310 is slightly convex as it faces the opposing occluding surface 316. Again, occluding surface 316 is non-planar. The contact edge 336 which is a circular line, minimizes the contact area and thus the possibility of occlusion due to particulate matter. In this situation, the occluding surface 316 is a conical concave surface of revolution. This is unlike the non-planar surface in FIG. 2 which was a concave curvilinear surface of revolution. Both of them will present a surface that the flexible diaphragm 310 or 210 in FIGS. 3 and 2, respectively, will contact on a line edge. FIG. 3 also illustrates the concept that a central stem represented by 330 can be drawn through the hole 350 in part of the structure of the firm body 307. The hole 308 and 308' represent the fluid access holes through the firm body portion 307 for the fluid to exert pressure and flow past the occluding surface 335 of the diaphragm 310.

Both illustrations in FIG. 2 and FIG. 3 show either a planar or slightly convex shape of diaphragm opposing the occluding surface, and this is different from previous designs which show arch-shaped or convex diaphragms facing the occluding surface. An advantage of the diaphragm shape in FIGS. 2 and 3 of the present invention is that they can be examined readily by flatness testing means to show the degree or non-degree of their deformation and thus pressure against the occluding surface. This will be a measure of the amount of pre-load that is put on the diaphragm and thus of the pressure flow characteristics which the diaphragm will give rise to.

Figure 4:
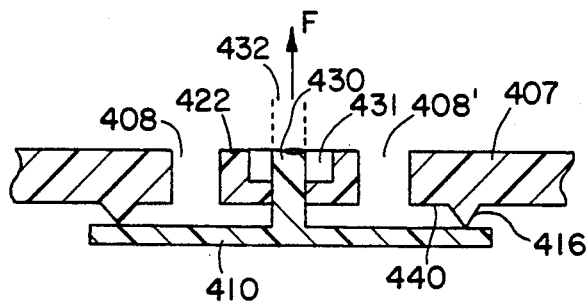
FIG. 4 shows another embodiment of the pressure flow element of the present invention in which a planar diaphragm achieves occlusion against the opposing surface where the opposing surface has a non-planar annular ridge which contacts the diaphragm on a narrow area.

Returning to the construction of the stem 330 in FIG. 3. That stem can be drawn through the hole 350 and the extension of the stem 332 can later be cut off to save space. The stem may actually be put under tension by a calibrated amount so that the diaphragm 310 will achieve a certain degree of force on the occluding surface 316 or alternatively achieve a certain degree of deformation or convexity. Once the stem 332 has been so biased, it may be secured or glued in place by inserting glue into the region 331 around the stem. Once the glue has frozen the stem in place, the diaphragm will be pre-loaded. A variety of manufacturing methods could achieve a degree of pre-load according to the pressure flow characteristics that wish to be achieved. For example, the diaphragm could be assembled in an orientation inverted from what is shown in FIG. 2 and a certain amount of weight can be hung on the stem to pre-load it in a calibrated way. Gluing could then take place with this pre-load in place. Alternatively, the stem could have predetermined enlargement areas in it so that when drawn through the hole 350, the stem will tend to register itself relative to the hole in a predetermined position. It is also clear that the durometer or resilience of the rubber that is used to make the diaphragm 310 can be so adjusted to give a certain degree of compliance to that diaphragm as desired. Another alternative method of varying the compliance of the diaphragm is to thicken the diaphragm either uniformly or in a graded fashion from the center to the periphery to achieve a certain modulus of elasticity as wished. FIG. 4 shows yet another embodiment of the pressure flow control element of the present invention. Here, a planar diaphragm 410 is drawn by its stem 432 through the hole structure in element 422 and glued in place by the material in space 431. The occluding surface of element 407 is now not completely concave but has an annular ridge, indicated by 416, that contacts the outer margin of the diaphragm 410. As in the previous figures, the occlusion is achieved along a circular line between the diaphragm upper surface and the nearly linear ridge represented by structure 416. This is a convenient geometry for testing since, by looking edgewise on such an assembly, one can easily check the contact of the diaphragm 410 along its lip with the occluding surface 416. Also, the degree of deformation of the diaphragm under pre-load can be examined and measured so as to calibrate the system in a configurational sense. Such physical calibration is difficult with concave diaphragms or arch-shaped diaphragms as taught in the patents of Heyer-Schulte and Pudenz-Schulte referred to above. We have indicated by the arrow and this symbol F that a force will be applied to the stem 432 during assembly to pre-load the diaphragm.

Figure 5:
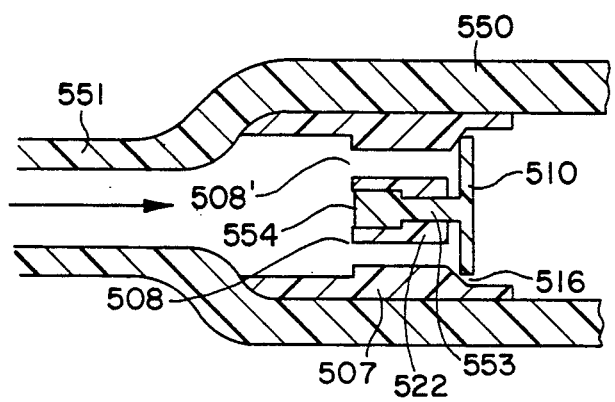
FIG. 5 shows another embodiment of the planar diaphragm, non-planar occluding surface, in a low profile, cylindrical shunt geometry.

FIG. 5 shows yet another embodiment of the present invention involving a substantially planar diaphragm, in this case in an axial geometry where the proximal end of an encasing body 551 accesses the ventricular space. The flow is in this case nearly linear through the holes 508 and 508' to the pressure control element 510 as described in the previous figures. This geometry or pressure control element would be particularly suitable for cylindrical inline type valve structures.

Figure 6:
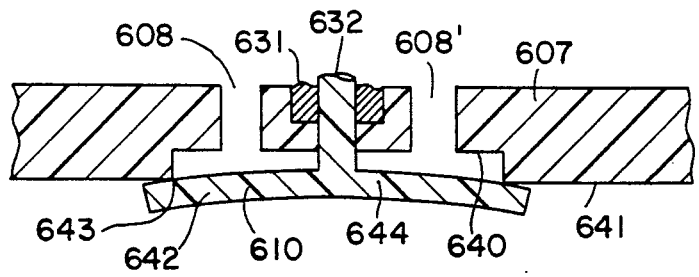
FIG. 6 shows yet another embodiment of the present invention in which the substantially planar diaphragm is put under tension to give it a somewhat convex shape, and it contacts the non-planar opposing surface on a step-like ridge, the rest of that surface being a pocket beneath the mushroom-shaped diaphragm area.

FIG. 6 shows another embodiment of the present pressure flow construction wherein the diaphragm 610 has again a slightly convex shape and contacts the opposing rigid structure 607 along a ridge at the lip indicated by 643. The shape of the structure 607 just beneath the diaphragm is concave and has in this case a cylindrical cavity with a relatively sharp edge, as opposed to a curvilinear, beveled or cone-shaped cavity in FIGS. 2, 3, and 5. This configuration may be desirable in some contexts, as it is relatively easy to make a square section cylindrical cavity as shown in a molding process. Here tight quality control could be made on the cavity to assure concentricity relative to the central hole in element 631 and with regard to flatness and flash-free character.

Figure 7:
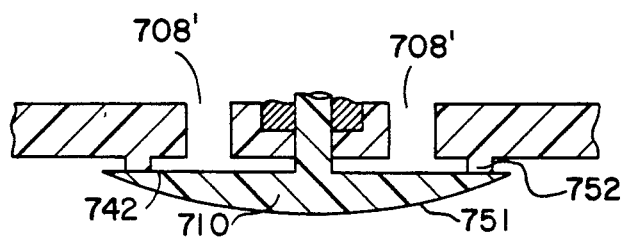
FIG. 7 shows another embodiment of the pressure control element to this invention in which the diaphragm is non-arched-shaped and has a thickened center portion to change the pressure flow characteristics.

FIG. 7 shows another embodiment of the present invention in which the diaphragm 710 has a flat occluding surface 742, but it has a non-planar, curved outer surface 751. This means that the central section of the diaphragm is thicker than the outer edge. This is a way of changing the deflection characteristic of the diaphragm as a function of fluid pressure on opposite sides. This in turn will change the pressure flow characteristics of the shunt valve. We also note that the opposing, occluding surface is non-planar and has a concave cavity. The lip 752 is the only portion which contacts the diaphragm 751 on its inner surface 742. The rest of the opposing surface is set back from the diaphragm so that it will not contact it in ordinary usage. This can have an advantage that the actual valve occlusion surfaces are approximating a very small annulus, representing the contact with lip or protrusion 752.

The diaphragm, as shown in FIGS. 1-7, is either planar on its occluding surface or slightly convex as one looks from the opposing surface. This is different from previous inventions where they have devised arch-shaped diaphragms for this purpose. It is also worth noting that the diaphragms have a central stem so that they are "mushroom-shaped" in their character, and yet they do not have a concave or arch-shaped section view through the diaphragm itself, as was claimed in the Pudenz-Schulte patents.

There are obviously many other variations on the present invention which one skilled in the art could draw. A non-concave diaphragm having a cusp shape or variation in thickness has already been discussed. A variety of materials could be used and methods of manufactured quality control could be described and implemented. The manufacturing process of the diaphragm may be critical for consistency and proper compliance characteristics of the pressure control element. For example, selection of proper silicone rubber to be used in the diaphragm is important. The molding procedure is also important. For example, the pre-loading of a compression mold is critical in achieving a uniformity of pressure and stress throughout the molded part so that the piece comes out flat and uniform without distortion. The proper durometer of the silicone rubber used in the diaphragm is also important, and this can be graded depending on the stiffness that one wishes to achieve in the diaphragm. The testing of diaphragms and sample selection of diaphragms based on their stiffness is a method of assuring that the proper pressure flow characteristics will be achieved. Pre-testing of the diaphragms in a test arrangement can be done before they are permanently glued into the base structure. For example, the diaphragms themselves could be put into a pre-loaded situation on a simulating occluding surface, the pressure flow characteristics thereby determined and measured, and the associated biasing or force applied to achieve the desired pressure flow characteristics when the actual gluing procedure is done.

Any of the diaphragm designs in FIGS. 2-6 can be installed in the distal base element of the invention shown FIG. 1. The concept of having separated proximal and distal base elements as shown in FIG. 1 and discussed above, has another notable advantage. As described above, not only does this design lend itself to an articulating geometry for the shunt, but it also lends itself to modularity for installation of identical components in different shunt configurations. For example, referring to FIG. 1, the base structure 3 with pressure control element and the distal connector 5 could be used in several configurations of shunts with different sized silicone housings such as 12 and silicone bases such as 15. Thus, a pediatric or adult-sized shunt can be made with the same distal base element. The same comment could be made about the proximal base element with its occluding port. Thus there is an economic advantage in the modular and separable base elements as described in the present invention and shown specifically in FIG. 1. Manufacturing economy is also achieved by having such interchangeable, modular elements.

Having described the various embodiments of the present invention, what we wish to secure by U.S. Letters Patent are the following Claims:

We claim:

1. A shunt valve for the shunting and pressure regulation of cerebrospinal fluid from the ventricles of the brain, said shunt valve comprising:
   A. a proximal end portion and a distal end portion;
   B. a proximal body at the proximal end portion adapted for connection to a proximal catheter, said proximal body having a proximal port;
   C. a distal body at said distal end portion of said shunt valve device adapted for connection to a distal catheter, said distal body having a distal port;
   D. a flexible housing having:
      (i) a proximal section located over said proximal port and cooperatively configured relative to said proximal port so that deflection of said proximal section will occlude said proximal port
      (ii) a distal section located over said distal port and cooperatively configured relative to said distal port so that deflection of said distal section will occlude said distal port and,
      (iii) a flexible middle section positioned between said proximal section and said distal section to form a chamber;
   said flexible housing, said distal body, and said proximal body being cooperatively configured and so adapted to form a fluid channel between said proximal end portion and said distal end portion, and so that said proximal port will occlude said fluid channel when said flexible housing proximal section is deflected, and so that said distal port will occlude said fluid channel when said flexible housing distal section is deflected; whereby the overall shape of said shunt valve can change upon implantation of the shunt valve to conform to the contours of the body in which it is implanted; and,
   E. a pressure control element having:
      (i) a substantially planar diaphragm which deflects with change in fluid pressure of fluid in said fluid channel across said substantially planar diaphragm; and,
      (ii) an opposing occluding element with a non-planar occluding surface in the regions where said opposing occluding element contacts said substantially planar diaphragm for a pre-determined pressure relationship of said fluid on opposing sides of said substantially planar diaphragm.

2. A shunt valve for the shunting and pressure regulation of cerebrospinal fluid from the ventricles of the brain, said shunt valve comprising:
   A. a proximal end portion and a distal end portion;
   B. a proximal body at the proximal end portion adapted for connection to a proximal catheter, said proximal body having a proximal port;
   C. a distal body at said distal end portion of said shunt valve device adapted for connection to a distal catheter, said distal body having a distal port;
   D. a flexible housing having:
      (i) a proximal section located over said proximal port and cooperatively configured relative to said proximal port so that deflection of said proximal section will occlude said proximal port
      (ii) a distal section located over said distal port and cooperatively configured relative to said distal port so that deflection of said distal section will occlude said distal port and,
      (iii) a flexible middle section positioned between said proximal section and said distal section to form a chamber;
   said flexible housing, said distal body, and said proximal body being cooperatively configured and so adapted to form a fluid channel between said proximal end portion and said distal end portion, and so that said proximal port will occlude said fluid channel when said flexible housing proximal section is deflected, and so that said distal port will occlude said fluid channel when said flexible housing distal section is deflected; whereby the overall shape of said shunt valve can change upon implantation of the shunt valve to conform to the contours of the body in which it is implanted; and,
   E. a pressure control element having:
      (i) a non-arch-shaped diaphragm which moves with change of fluid pressure on opposing sides; and,
      (ii) an opposing, occluding element with a non-planar and in part concave occluding surface in the region which opposes said non-arch-shaped diaphragm so that when said non-arch-shaped diaphragm contacts said opposing occluding element, it will stop the flow of fluid past said non-arched-shaped diaphragm, and said opposing occluding element will not contact said non-arched-shaped element diaphragm over said concave surface.

3. The shunt valve of claim 2 wherein said in part concave occluding surface is a curvelinear surface of revolution.

4. The shunt valve of claim 2 wherein said in part concave occluding surface is a conical surface of revolution.

5. The shunt valve of claim 2 wherein said in part concave occluding surface is a beveled surface.

6. A shunt valve for the shunting and pressure regulation of cerebrospinal fluid from the ventricles of the brain, said shunt valve comprising:
   A. a proximal end portion and a distal end portion;
   B. a proximal body at the proximal end portion adapted for connection to a proximal catheter, said proximal body having a proximal port;
   C. a distal body at said distal end portion of said shunt valve device adapted for connection to a distal catheter, said distal body having a distal port;
   D. a housing having:
      (i) a proximal section located over said proximal port and cooperatively configured relative to said proximal port so that deflection of said proximal section will occlude said proximal port
      (ii) a distal section located over said distal port and cooperatively configured relative to said distal port so that deflection of said distal section will occlude said distal port and,
      (iii) a middle section positioned between said proximal section and said distal section to form a chamber;
   said housing, said distal body, and said proximal body being cooperatively configured and so adapted to form a fluid channel between said proximal end portion and said distal end portion, and so that said proximal port will occlude said fluid channel when said housing proximal section is deflected, and so that said distal port will occlude said fluid channel when said housing distal section is deflected;
   E. a pressure control element having:
      (i) a substantially planar diaphragm which deflects with change in fluid pressure of fluid in said fluid channel across said substantially planar diaphragm; and,
      (ii) an opposing occluding element with a non-planar occluding surface in the regions where said opposing occluding element contacts said substantially planar diaphragm for a pre-determined pressure relationship of said fluid on opposing sides of said substantially planar diaphragm.

7. A shunt valve for the shunting and pressure regulation of cerebrospinal fluid from the ventricles of the brain, said shunt valve comprising:
   A. a proximal end portion and a distal end portion;
   B. a proximal body at the proximal end portion adapted for connection to a proximal catheter, said proximal body having a proximal port;
   C. a distal body at said distal end portion of said shunt valve device adapted for connection to a distal catheter, said distal body having a distal port;
   D. a housing having:
      (i) a proximal section located over said proximal port and cooperatively configured relative to said proximal port so that deflection of said proximal section will occlude said proximal port
      (ii) a distal section located over said distal port and cooperatively configured relative to said distal port so that deflection of said distal section will occlude said distal port and,
      (iii) a middle section positioned between said proximal section and said distal section to form a chamber;
   said housing, said distal body, and said proximal body being cooperatively configured and so adapted to form a fluid channel between said proximal end portion and said distal end portion, and so that said proximal port will occlude said fluid channel when said housing proximal section is deflected, and so that said distal port will occlude said fluid channel when said housing distal section is deflected;
   E. a pressure control element having:
      (i) a non-arch-shaped diaphragm which moves with change of fluid pressure on opposing sides; and,
      (ii) an opposing, occluding element with a non-planar and in part concave occluding surface in the region which opposes said non-arch-shaped diaphragm so that when said non-arch-shaped diaphragm contacts said opposing occluding element, it will stop the flow of fluid past said non-arched-shaped diaphragm, and said opposing occluding element will not contact said non-arched-shaped element diaphragm over said concave surface.

8. The shunt valve of claim 7 wherein said in part concave occluding surface is a curvelinear surface of revolution.

9. The shunt valve of claim 7 wherein said in part concave occluding surface is a conical surface of revolution.

10. The shunt valve of claim 7 wherein said in part concave occluding surface is a beveled surface.